US010702680B2

(12) United States Patent
Chen et al.

(10) Patent No.: US 10,702,680 B2
(45) Date of Patent: Jul. 7, 2020

(54) METHOD OF OPERATING AN INTEGRATED BALLOON CATHETER INFLATION SYSTEM

(71) Applicant: Edwards Lifesciences Corporation, Irvine, CA (US)

(72) Inventors: Harvey H. Chen, Irvine, CA (US); Andrew Phung, Brea, CA (US); Thomas H. Chien, San Jose, CA (US); Da-Yu Chang, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 290 days.

(21) Appl. No.: 15/925,086

(22) Filed: Mar. 19, 2018

(65) Prior Publication Data

US 2018/0207411 A1    Jul. 26, 2018

Related U.S. Application Data

(63) Continuation of application No. 14/469,978, filed on Aug. 27, 2014, now Pat. No. 9,919,137.

(60) Provisional application No. 61/871,240, filed on Aug. 28, 2013.

(51) Int. Cl.
  *A61M 25/10* (2013.01)
  *A61F 2/24* (2006.01)
  *A61M 25/00* (2006.01)

(52) U.S. Cl.
  CPC ..... *A61M 25/10185* (2013.11); *A61F 2/2433* (2013.01); *A61M 25/10181* (2013.11); *A61M 25/10184* (2013.11); *A61M 25/0097* (2013.01)

(58) Field of Classification Search
  CPC ............ A61F 2/2433; A61M 25/1018; A61M 25/10184; A61M 25/10185; A61M 25/0097
  See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |

(Continued)

*Primary Examiner* — Alexander J Orkin
(74) *Attorney, Agent, or Firm* — Guy Cumberbatch

(57) ABSTRACT

An inflation system having two pressure vessels integrated into a balloon catheter. A pressurized chamber and a vacuum chamber are integrally attached to proximal end of the balloon catheter and activated by a common valve or switch. Pressure or vacuum is selectively transmitted to the balloon depending on the valve/switch position. The working fluid may be air, or a combination of air and saline with an intermediate piston/cylinder assembly. The balloon catheter may be a part of a heart valve delivery system with a balloon-expandable heart valve crimped onto the balloon.

20 Claims, 2 Drawing Sheets

(56) References Cited

U.S. PATENT DOCUMENTS

| | | |
|---|---|---|
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,270,527 A | 6/1981 | Peters et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,598,707 A | 7/1986 | Agdanowski et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,758,223 A | 7/1988 | Rydell |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,135,026 A | 8/1992 | Manska |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,336,183 A | 8/1994 | Greelis et al. |
| 5,344,397 A | 9/1994 | Heaven et al. |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,669,879 A | 9/1997 | Duer |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,749,853 A | 5/1998 | O'Donnell et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,885,244 A | 3/1999 | Leone et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,073,291 A | 6/2000 | Davis |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,241,706 B1 | 6/2001 | Leschinsky et al. |
| 6,264,611 B1 | 7/2001 | Ishikawa et al. |
| 6,322,526 B1 | 11/2001 | Rosenman et al. |
| 6,350,282 B1 | 2/2002 | Eberhardt |
| 6,491,624 B1 | 12/2002 | Lotfi |
| 6,773,457 B2 | 8/2004 | Ivancev et al. |
| 7,037,333 B2 | 5/2006 | Myers et al. |
| 7,041,056 B2 | 5/2006 | Deslauriers et al. |
| 7,195,610 B1 | 3/2007 | Flachbart |
| D581,967 S | 12/2008 | Murray |
| 7,527,605 B2 | 5/2009 | Evans |
| 7,998,151 B2 | 8/2011 | St. Goar et al. |
| 8,114,154 B2 | 2/2012 | Righini et al. |
| 8,273,120 B2 | 9/2012 | Dolan |
| 8,308,798 B2 | 11/2012 | Pintor et al. |
| 8,323,337 B2 | 12/2012 | Gurskis et al. |
| 8,348,998 B2 | 1/2013 | Pintor et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |

(56) References Cited

U.S. PATENT DOCUMENTS

| | | |
|---|---|---|
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0078538 A1 | 4/2003 | Neale et al. |
| 2003/0079752 A1 | 5/2003 | Hart et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260237 A1 | 12/2004 | Squadrito |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0063973 A1 | 3/2006 | Makower et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010787 A1 | 1/2007 | Hackett et al. |
| 2007/0010788 A1 | 1/2007 | Evans |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |

(56) References Cited

U.S. PATENT DOCUMENTS

| | | |
|---|---|---|
| 2007/0288089 A1 | 12/2007 | Gurskis et al. |
| 2007/0293942 A1 | 12/2007 | Mirzaee |
| 2008/0021546 A1 | 1/2008 | Patz et al. |
| 2008/0033543 A1 | 2/2008 | Gurskis et al. |
| 2008/0065011 A1 | 3/2008 | Marchand et al. |
| 2008/0065198 A1 | 3/2008 | Quintessenza |
| 2008/0119875 A1 | 5/2008 | Ino et al. |
| 2008/0154356 A1 | 6/2008 | Obermiller et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0069890 A1 | 3/2009 | Suri et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0161036 A1 | 6/2010 | Pintor et al. |
| 2010/0198249 A1 | 8/2010 | Sabliere |
| 2010/0241178 A1 | 9/2010 | Tilson et al. |
| 2010/0249894 A1 | 9/2010 | Oba et al. |
| 2010/0249908 A1 | 9/2010 | Chau et al. |
| 2010/0331972 A1 | 12/2010 | Pinter et al. |
| 2011/0011474 A1 | 1/2011 | Duncan |
| 2011/0022165 A1 | 1/2011 | Oba et al. |
| 2011/0144690 A1 | 6/2011 | Bishop et al. |
| 2011/0147251 A1 | 6/2011 | Hodshon et al. |
| 2011/0270224 A1 | 11/2011 | Ehrenreich et al. |
| 2011/0288478 A1 | 11/2011 | Ehrenreich et al. |
| 2012/0065729 A1 | 3/2012 | Pintor et al. |
| 2012/0078096 A1 | 3/2012 | Krolik et al. |
| 2012/0150288 A1 | 6/2012 | Hodshon et al. |
| 2012/0157832 A1 | 6/2012 | Feigenwinter et al. |
| 2012/0239046 A1 | 9/2012 | Kaiser et al. |
| 2012/0310334 A1 | 12/2012 | Dolan |
| 2013/0053949 A1 | 2/2013 | Pintor et al. |
| 2013/0060316 A1 | 3/2013 | Sanati et al. |
| 2013/0116777 A1 | 5/2013 | Pintor et al. |
| 2013/0190796 A1 | 7/2013 | Tilson et al. |
| 2014/0088362 A1 | 3/2014 | Terliuc et al. |

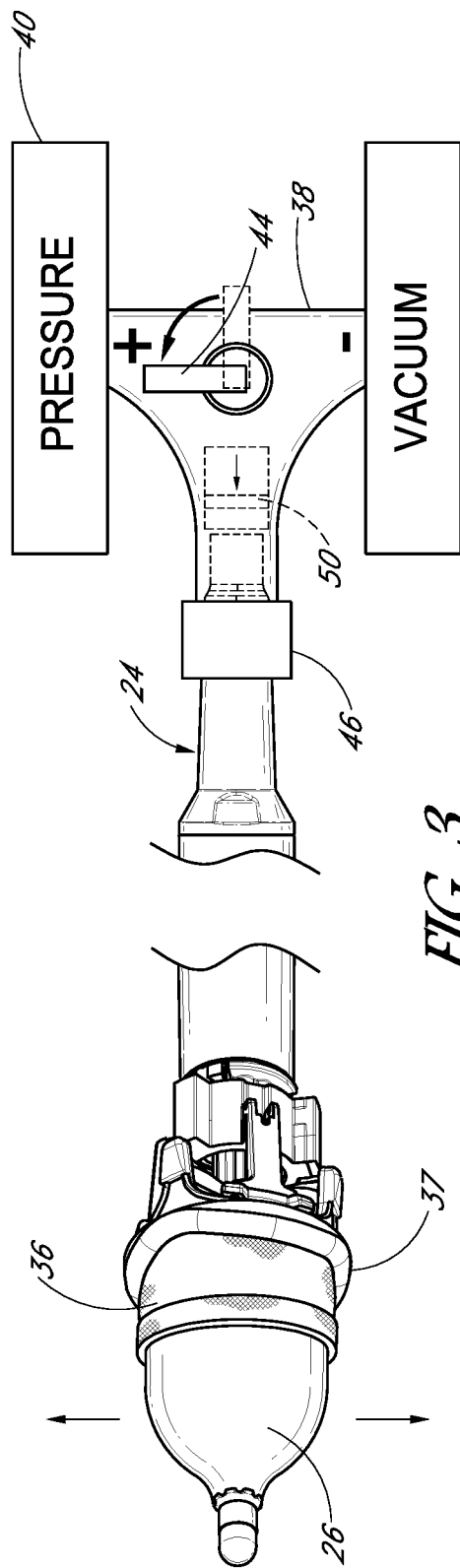
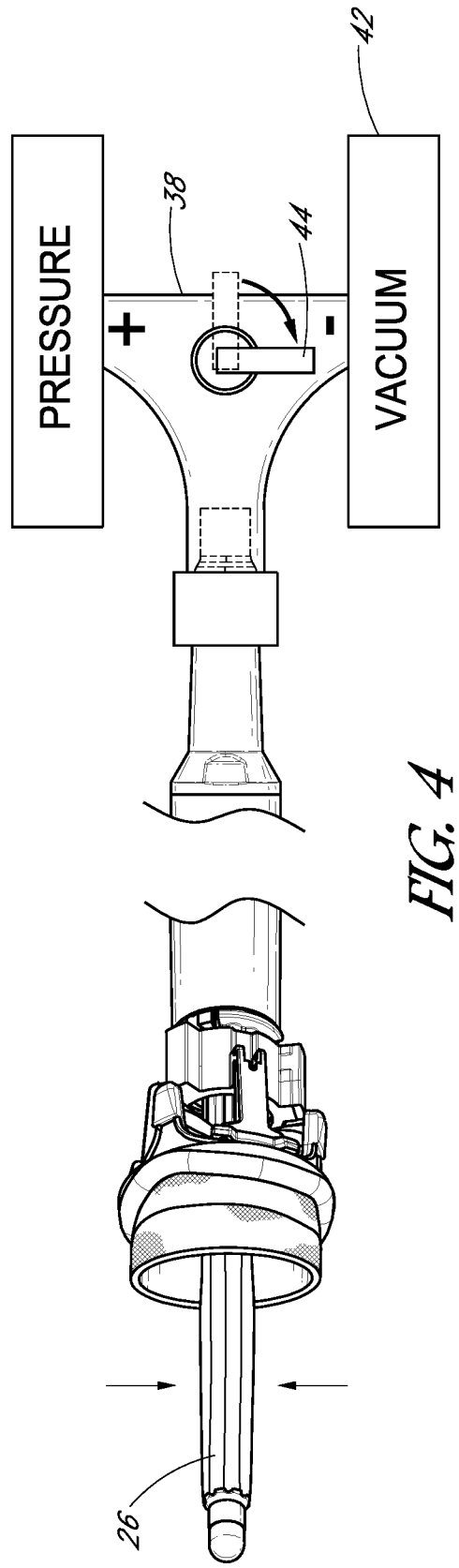
FIG. 3
FIG. 4

METHOD OF OPERATING AN INTEGRATED BALLOON CATHETER INFLATION SYSTEM

CROSS REFERENCE TO RELATED APPLICATIONS

This application is a continuation of U.S. application Ser. No. 14/469,978, filed Aug. 27, 2014, now U.S. Pat. No. 9,919,137, which claims the benefit of U.S. Application No. 61/871,240, filed Aug. 28, 2013, the entire disclosures all of which are incorporated by reference.

FIELD OF THE INVENTION

The present invention generally relates to balloon catheters and, in particular, to an integrated inflation system for balloon catheters.

BACKGROUND OF THE INVENTION

Balloon dilatation catheters are used for a variety of procedures in which a body lumen or vessel is dilated. For example, such catheters are used in percutaneous transluminal angioplasty procedures in which a stenosed region of an artery, such as a coronary artery, is widened by inserting a deflated balloon into the stenosis and then inflating the balloon under pressure to forcibly enlarge the lumen through the artery. After a brief period of time, the balloon is deflated and removed. Such catheters typically have an elongate flexible shaft and a balloon mounted at the distal end of the shaft. The shaft has a balloon inflation lumen that provides fluid communication between the proximal end of the catheter and the interior of the balloon at the distal end of the shaft.

Balloon catheters are typically actuated by manual syringes, often called "inflators" (or inflation devices), which use a plunger that is manually advanced using a rod that is threaded into a handle to allow the operator to advance the plunger using very small, controlled increments. Some syringes include a pressure gauge, but the gauge is often located on the syringe itself, and it therefore may be impractical for the physician to monitor the gauge as he or she tries to also watch an image of the balloon being inflated on a monitor. The process for setting up and operating a manual balloon inflation syringe creates logistical difficulties.

Automatic injection devices, such as described in U.S. Pat. No. 6,099,502, are known for delivering fluids such as saline and contrast agents through a catheter to a patient. The devices typically include a motor-driven linear actuator that forces a plunger through a syringe, thereby creating a desired fluid flow into the patient. For sanitation purposes, the syringe and all associated tubing between the patient and the syringe are disposable, which increases the expense of the system. Further, preparing the automatic injection device for operation can be a time-consuming process. Various tubes may need to be connected together and to the device. The operator preparing the injection device for operation must often be careful to ensure that the connections are tight and that none of the tubes are pinched or otherwise blocked.

Although numerous configurations are available for inflating balloon catheters, there is a need for a simpler system.

SUMMARY OF THE INVENTION

An integrated inflation system having two pressure vessels integrated into a balloon catheter. A pressurized chamber and a vacuum chamber are integrated within the proximal end of the balloon catheter and activated by a common valve or switch. Pressure or vacuum is transmitted to the balloon depending on the valve/switch position.

In one embodiment, a balloon catheter system having an integrated inflation subsystem, comprises a manifold having internal passages and a pressurized vessel integrated with an inflation port in the manifold. A balloon catheter has a balloon on a distal end in fluid communication with an inflation lumen extending through the catheter, which in turn is in fluid communication with a balloon port in the manifold. A control valve on the manifold is configured to selectively open and close fluid communication between the balloon port and the inflation port so that a positive pressure differential from the pressurized vessel inflates the balloon. The system may further include a vacuum vessel integrated with a vacuum port in the manifold, wherein the control valve is also configured to selectively open and close fluid communication between the balloon port and the vacuum port so that a negative pressure differential from the vacuum vessel deflates the balloon.

In accordance with another aspect, a manufactured balloon catheter system includes a balloon catheter having a balloon on a distal end in fluid communication with an inflation lumen extending through the catheter, and an integrated inflation system assembled and packaged with the balloon catheter. The integrated inflation system has a manifold with internal passages, a pressurized vessel integrated with an inflation port in the manifold, a vacuum vessel integrated with a vacuum port in the manifold, and a balloon port in the manifold in fluid communication with the balloon catheter inflation lumen. Finally, a control valve on the manifold selectively opens fluid communication between the manifold port and one or the other of the pressurized vessel and vacuum vessel.

In a preferred embodiment, the balloon catheter system is part of a prosthetic heart valve delivery system including a balloon-expandable heart valve crimped onto the balloon. Desirably, the pressurized vessel and the vacuum vessel are permanently attached to the manifold, such as via adhesion or thermal welding. In a preferred version, the manifold opens to just the balloon port, inflation port and vacuum port, and the control valve is a stopcock mounted for rotation on the manifold into three positions. The system may further include a pressure regulator located between the control valve and the balloon to limit a balloon pressure to a predetermined maximum. Preferably, the pressurized vessel holds air, and the system may further include a piston/cylinder assembly incorporated into the manifold on which the pressurized air acts and saline is provided in the system distal to the piston/cylinder assembly for inflating the balloon.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 3 shows inflation of the balloon to expand the heart valve stent by opening communication between a pressure vessel and the balloon; and FIG. 4 shows deflation of the balloon for withdrawal from within the heart valve stent by opening communication between a vacuum vessel and the balloon.

DETAILED DESCRIPTION OF THE PREFERRED EMBODIMENTS

The present application discloses an integrated inflation system for a balloon catheter. The inflation system can be coupled to any type of balloon catheter, including but not limited to those used for angioplasty, vascular stent expansion, or as in the illustrated embodiment, expansion of a prosthetic heart valve stent. The term "integrated" refers to a manufactured assembly of components that enable rapid inflation and deflation of the balloon of the catheter. An integrated system is not simply an assembly of components, but rather components that have been pre-assembled during the fabrication process so that they are packaged and sold as a single, unitary system. In this sense, "integrated" contemplates systems that are pre-assembled as one product, and packaged and stored in a unique enclosure as opposed to two or more. Thus, an integrated system arrives at the operating site complete with no further connections needed. The components may be "permanently" joined together, such as by being adhered or thermal welded together so that they cannot be separated without damaging the system, though the components can also be connected together through less permanent means such as with threaded connectors or the like. Other "permanent" connections include a configuration where the components are molded together as one piece, or where some components are "within" larger components, such as where a pressure vessel is positioned within a manifold. Of course, "permanently" connecting components does not mean that they cannot ever be separated, such as with brute force, but rather that they are not intended to be separated and that separation will damage their ready functionality in some way.

Figure 1:
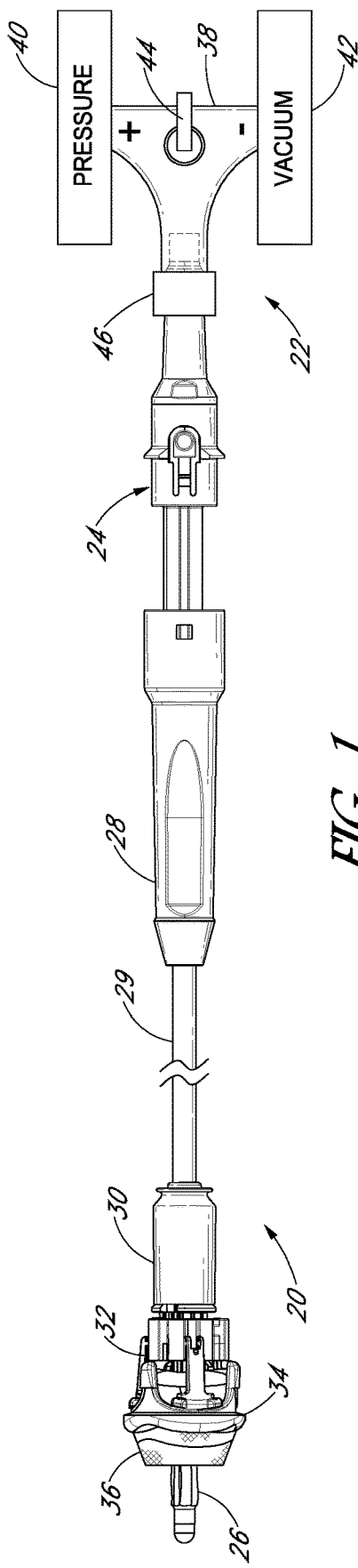
FIG. 1 is a top plan view of a prosthetic heart valve delivery system including a balloon catheter and introducer combination, with an integrated inflation system on the proximal end of the balloon catheter.

FIG. 1 illustrates a prosthetic heart valve delivery system 20 having an integrated inflation system 22 on the proximal end of a balloon catheter 24 which terminates on a distal end in an expandable balloon 26. In the illustrated system 20, the balloon catheter 24 slides linearly within a handpiece of an introducer 28. The introducer 28 also has a malleable handle shaft 29 leading to a distal locking sleeve 30. The locking sleeve 30 couples to a valve holder 32 that in turn secures a prosthetic heart valve 34 having a distal anchoring stent 36. The entire system has a length from the proximal end of the inflation system 22 to the tip of the balloon 26 that may vary depending on the implant technique. For example, devices for surgical valve replacement require relatively short catheters, perhaps between about 200 and 400 mm. On the other hand, so-called "direct-access" devices for beating heart surgeries enter the body through a port in the chest and are routed essentially directly to the heart, requiring somewhat longer catheters, perhaps 300 to 600 mm. Finally, transfemoral deliveries that enter through the leg and pass through the vasculature require much longer catheters, often between 100-200 cm.

Figure 2:
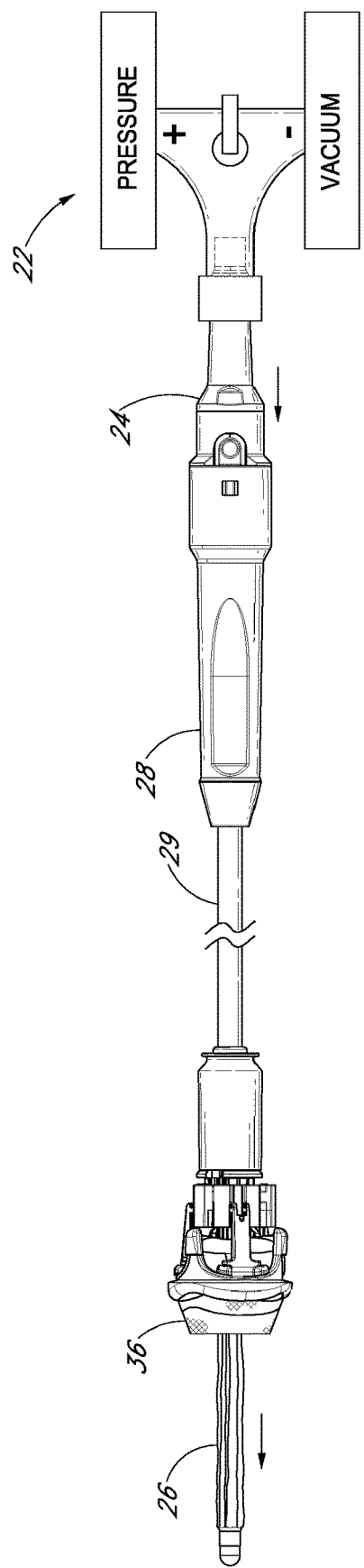
FIG. 2 shows the prosthetic heart valve delivery system with the balloon catheter advanced relative to the introducer to position an expansion balloon within a heart valve stent.

The balloon 26 is initially retracted within the introducer 28 and heart valve 34, and distal movement of the balloon catheter 24 as seen in FIG. 2 moves the balloon 26 into a predetermined position to enable expansion of the heart valve stent 36. As will be explained, inflation of the balloon 26 expands the heart valve stent 36 outward into contact with surrounding anatomy. The prosthetic heart valve delivery system 20 is particularly well-suited for implanting a prosthetic aortic valve at an aortic annulus, with the stent 36 positioned sub-annularly, against the left ventricular wall adjacent the aortic valve annulus. Additional details of the exemplary valve deployment system 20 and method of use are disclosed in U.S. Pat. No. 8,641,757, filed Jun. 23, 2011, the contents of which are expressly incorporated by reference herein. A commercial system having many of the same components is sold as the EDWARDS INTUITY valve system by Edwards Lifesciences Corp. of Irvine, Calif.

The integrated inflation system 22 includes a junction manifold 38 having internal passages and at least three inlet/outlet ports, one of which connects to the proximal end of the balloon catheter 24 (a balloon port). A second inlet/outlet port, or inflation port, of the manifold 38 connects to a sealed pressure vessel 40, while a third inlet/outlet port, or vacuum port, connects to a sealed vacuum vessel 42. A control valve in the form of a stopcock 44 mounted in the manifold 38 controls which of the inlet/outlet ports are in fluid communication. In a preferred embodiment the manifold 38 opens to just the balloon port 24, inflation port, and vacuum port, and the control valve is a manual stopcock mounted for rotation on the manifold into three positions. It should be understood that the stopcock 44 represents a fluid control valve that can be an electromechanical valve having a switch, solenoids, or other such devices, and thus the term "control valve" should not be considered limited to a purely mechanical/manual stopcock. The inflation system 22 further includes a pressure regulator 46 interposed between the manifold 38 and the balloon catheter 24. The pressure regulator 46 functions to sense pressure in the lumen of the balloon catheter 24 and close upon reaching a threshold pressure.

The particular pressure used to inflate the balloon 26 varies depending on the application. For instance, the exemplary pressure used in the EDWARDS INTUITY valve system is between about 4.5-5 atmospheres (0.46-0.51 MPa). Other systems may require more or less pressure, such as up to 7 atm (0.71 MPa), or may utilize a volume based inflation criteria to achieve a specific diameter. In the latter case, the pressure regulator 46 may be replaced or supplemented with a volumetric flow meter that indicates total volume delivered as opposed to pressure.

FIGS. 3 and 4 illustrate expansion and deflation of the balloon 26 to expand the anchoring stent 36. Initially, the stopcock is in a neutral position in between plus (+) and minus (−) signs printed, inscribed or embossed on the manifold 38. The neutral position closes off communication between any two ports of the manifold 38. The plus sign lies toward the pressure vessel 40, while the minus sign is adjacent to vacuum vessel 42. The plus and minus signs correspond respectively to expansion/inflation and contraction/deflation of the balloon 26 on the balloon catheter 24. Of course, other indicators such as the colors green and red may be provided on the manifold 38 for the same purpose. Furthermore, the vessels themselves may have the words "Pressure" and "Vacuum" (or Inflate/Deflate) printed, inscribed or embossed thereon, as shown.

FIG. 3 shows the stopcock 44 rotated CCW toward the pressure vessel 40 so as to open communication between the pressure vessel and the balloon catheter 24, thus causing the balloon 26 to inflate and expand, deploying the anchoring stent 36 against the annulus. The anchoring stent 36 transitions between its conical contracted state seen in FIGS. 1-2, and its generally tubular or slightly conical expanded state seen in FIGS. 3-4. Simple interference between the anchoring stent 36 and the annulus may be sufficient to anchor the heart valve 34, or interacting features such as projections, hooks, barbs, fabric, etc. may be utilized. Further, the heart valve 34 may have a sealing ring 37 which can be secured to the annulus using sutures, barbs, etc.

FIG. 4 shows the stopcock 44 rotated CW toward the vacuum vessel 42 which opens communication between the vacuum vessel and the balloon catheter 24. This communicates a reduced or negative pressure to the interior of the balloon 26, causing its deflation as shown. Deflation of the balloon 26 facilitates its removal from within the heart valve and the delivery system in general. It should be noted that not all balloon inflation systems require active deflation as shown. In those systems, a simple valve that enables passive deflation of the balloon pressure to the atmosphere may be provided. The vacuum vessel 42 could thus represent such a valve. While that may work with air as the working fluid, for saline it would be best to deflate the balloon actively.

The exemplary delivery system balloon 26 has a relatively high diameter-to-length ratio compared to other surgical balloons, such as those used to expand cardiovascular stents. This makes it particularly difficult for the balloon 26 to return to a small geometry upon deflation after deployment. Balloons of such size ratios tend to "butterfly" by forming wings that prevent removal through the valve 34 and its holder 32 without the application of high forces, which may cause damage to the valve itself. The exemplary balloon 26 thus preferably includes a series of longitudinal pleats heat set into its wall to facilitate self-collapse during deflation. Further, the distal end of the balloon 26 moves relative to the proximal end to enable lengthening of the balloon during deflation. This lengthening occurs automatically by virtue of an internal wire (not shown) which is spring-biased to stretch the balloon longitudinally. These components are also shown in U.S. Pat. No. 8,641,757. It should be noted that easy deflation and removal of the balloon 26 permits rapid replacement of the balloon catheter in case of a problem, such as insufficient inflation.

In the most basic configuration, the integrated inflation system 22 uses air as the working fluid to expand the balloon 26. However, air is typically only compatible for open procedures. In applications where controlled, pressurized, sterile physiologic saline is the working fluid, the system may require a dynamic piston against which air acts to cause the piston to displace the saline into the balloon 26. One of skill in the art will understand that such a piston/cylinder assembly can easily be incorporated into the manifold 38 between the stopcock 44 and the pressure regulator 46, such as shown schematically at 50 in FIG. 3.

The integrated inflation system 22, and in particular the pressure vessels 40, 42, are manufactured using metallic or polymer-based components, depending on the pressure loads. Desirably, the system 22 is assembled at the time of manufacture and packaged with the delivery system 20. As such, the pressure vessels 40, 42 will be required to maintain their respective internal pressures over long periods, sometimes years. Consequently, special seals between the pressure vessels 40, 42 and the manifold 38, and between the manifold 38 and the balloon catheter 24, are required. For example, the seals at the outlet of a recreational $CO_2$ cartridge may be suitable. Alternatively, welded or elastomeric seals which can be punctured or otherwise compromised at the time of use may be provided. Another solution is to provide a robust valve at the inlet/outlet of each pressure vessels 40, 42 that can be manually opened after the system has been removed from its sterile packaging just prior to use, thus initiating fluid communication between the vessels and the manifold 38 and stopcock 44.

While the invention has been described in its preferred embodiments, it is to be understood that the words which have been used are words of description and not of limitation. Therefore, changes may be made within the appended claims without departing from the true scope of the invention.

What is claimed is:

1. A method of storing and actuating a balloon catheter system, comprising:
providing an integrated pre-assembled system packaged and sold as a single, unitary system in a unique sterile enclosure, the system including:
a manifold having internal passages;
a sealed pressurized vessel permanently attached to an inflation port in the manifold;
a balloon catheter having a balloon on a distal end in fluid communication with an inflation lumen extending through the catheter;
a balloon port in the manifold in fluid communication with the balloon catheter inflation lumen; and
a control valve on the manifold configured to selectively open and close fluid communication between the balloon port and the inflation port so that a positive pressure differential from the pressurized vessel inflates the balloon;
the method including:
opening the unique sterile enclosure and removing the system;
advancing the balloon catheter so that the balloon thereon is positioned at a procedure site within the body; and
operating the control valve on the manifold to open fluid communication between the balloon port and the inflation port and inflate the balloon.

2. The method of claim 1, wherein the balloon catheter system is part of a prosthetic heart valve delivery system including a balloon-expandable heart valve crimped onto the balloon, and the step of advancing includes positioning the balloon-expandable heart valve within a native heart valve annulus.

3. The method of claim 1, further including a one-way valve attached to a deflation port in the manifold, wherein the control valve is also configured to selectively open and close fluid communication between the balloon port and the deflation port to enable passive deflation of the balloon pressure to the atmosphere, and the method includes operating the control valve to open fluid communication between the balloon port and the deflation port after inflating the balloon.

4. The method of claim 1, wherein the pressurized vessel is attached to the manifold in a manner selected from the group consisting of adhesion and thermal welding.

5. The method of claim 1, further including a sealed vacuum vessel permanently attached to a vacuum port in the manifold, wherein the control valve is also configured to selectively open and close fluid communication between the balloon port and the vacuum port so that a negative pressure differential from the vacuum vessel deflates the balloon, and the method includes operating the control valve to open fluid communication between the balloon port and the vacuum port after inflating the balloon.

6. The method of claim 5, wherein the manifold opens to just the balloon port, inflation port and vacuum port, and the control valve is a stopcock mounted for rotation on the manifold into three mutually exclusive positions.

7. The method of claim 5, further including provide a valve at an inlet/outlet of each of the sealed pressurized vessel and sealed vacuum vessel that must be manually opened after the system has been removed from the unique sterile enclosure, thus initiating fluid communication between the vessels and the manifold.

8. The method of claim 1, further including a pressure regulator located between the control valve and the balloon to limit a balloon pressure to a predetermined maximum.

9. The method of claim 1, further including an indicator printed, inscribed or embossed on the control valve that conveys information to a user regarding whether there is open fluid communication between the balloon port and the inflation port.

10. The method of claim 9, wherein the indicator is selected from the group consisting of:
a plus sign; and
the color green.

11. A method of storing and actuating a balloon catheter system, comprising:
providing an integrated pre-assembled system packaged and sold as a single, unitary system in a unique sterile enclosure, the system including:
a balloon catheter having a balloon on a distal end in fluid communication with an inflation lumen extending through the catheter;
an integrated inflation system having:
a manifold having internal passages;
a sealed pressurized vessel permanently attached to an inflation port in the manifold;
a sealed vacuum vessel permanently attached to a vacuum port in the manifold;
a balloon port in the manifold in fluid communication with the balloon catheter inflation lumen; and
a control valve on the manifold configured to selectively open and close fluid communication between the manifold internal passages and one or the other of the pressurized vessel and vacuum vessel;
the method including:
opening the unique sterile enclosure and removing the system;
advancing the balloon catheter so that the balloon thereon is positioned at a procedure site within the body;
operating the control valve on the manifold to open fluid communication between the balloon port and the inflation port and inflate the balloon;
operating the control valve on the manifold to close fluid communication between the balloon port and the inflation port and inflate the balloon;
operating the control valve on the manifold to open fluid communication between the balloon port and the vacuum port and deflate the balloon after inflating the balloon; and
withdrawing the balloon catheter from within the body.

12. The method of claim 11, wherein the balloon catheter system is part of a prosthetic heart valve delivery system including a balloon-expandable heart valve crimped onto the balloon, and the step of advancing includes positioning the balloon-expandable heart valve within a native heart valve annulus.

13. The method of claim 11, further including a one-way valve attached to a deflation port in the manifold, wherein the control valve is also configured to selectively open and close fluid communication between the balloon port and the deflation port to enable passive deflation of the balloon pressure to the atmosphere, and the method includes operating the control valve to open fluid communication between the balloon port and the deflation port after inflating the balloon.

14. The method of claim 11, wherein the pressurized vessel is attached to the manifold in a manner selected from the group consisting of adhesion and thermal welding.

15. The method of claim 11, wherein the manifold opens to just the balloon port, inflation port and vacuum port, and the control valve is a stopcock mounted for rotation on the manifold into three mutually exclusive positions.

16. The method of claim 11, further including provide a valve at an inlet/outlet of each of the sealed pressurized vessel and sealed vacuum vessel that must be manually opened after the system has been removed from the unique sterile enclosure, thus initiating fluid communication between the vessels and the manifold.

17. The method of claim 11, further including a pressure regulator located between the control valve and the balloon to limit a balloon pressure to a predetermined maximum.

18. The method of claim 11, further including an indicator printed, inscribed or embossed on the control valve that conveys information to a user regarding whether there is open fluid communication between the balloon port and the inflation port.

19. The method of claim 18, wherein the indicator is selected from the group consisting of:
a plus sign; and
the color green.

20. The method of claim 11, further including indicators printed, inscribed or embossed on the pressurized vessel and vacuum vessel selected from the group consisting of:
the word "Pressure" for the pressurized vessel and the word "Vacuum" for the vacuum vessel; and
the word "Inflate" for the pressurized vessel and the word "Deflate" for the vacuum vessel.

* * * * *